(12) United States Patent
Bett et al.

(10) Patent No.: US 6,856,859 B1
(45) Date of Patent: Feb. 15, 2005

(54) METHOD OF CONTROLLING CROSS-DIRECTION ALIGNMENT IN MANUFACTURING PROCESS

(75) Inventors: Thomas Arthur Bett, Oshkosh, WI (US); Tanakon Ungpiyakul, Neenah, WI (US); Shawn Timothy Lemery, South Ogden, UT (US); Russell Joseph Brumm, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 637 days.

(21) Appl. No.: 09/338,238

(22) Filed: Jun. 22, 1999

Related U.S. Application Data

(60) Provisional application No. 60/114,482, filed on Dec. 31, 1998.

(51) Int. Cl.[7] .............................................. G06F 7/00
(52) U.S. Cl. ........................................ 700/222; 700/59
(58) Field of Search ........................... 700/222, 59, 62, 700/110; 156/351; 226/15, 19, 20

(56) References Cited

U.S. PATENT DOCUMENTS

| | | | | |
|---|---|---|---|---|
| 3,332,681 A | * | 7/1967 | Gilbert | ..................... 270/30.07 |
| 3,373,912 A | * | 3/1968 | Toensing | ..................... 226/20 |
| 3,822,944 A | | 7/1974 | Hopkins et al. | ............. 356/152 |

(List continued on next page.)

FOREIGN PATENT DOCUMENTS

| | | | | |
|---|---|---|---|---|
| CA | 2044792 | 5/1992 | ............ | G05D/5/04 |
| EP | 0 485 691 B1 | 5/1992 | ............ | B26D/5/34 |
| EP | 0 485 691 A2 | 5/1992 | ............ | B26D/5/34 |

(List continued on next page.)

OTHER PUBLICATIONS

*Acquiring and Displaying Images*, COGNEX, pp. 34–35, 136–138, 143, 146–148, 153–154, and 530, date unknown.

"User's Manual Model 1012," *Kodak Ektapro EM Motion Analyzer*, Eastman Kodak Company, 1990. pp. 1.1–7.9.

*Primary Examiner*—James McClellan
(74) *Attorney, Agent, or Firm*—Jeffrey B. Curtin; Paul Y. Yee

(57) ABSTRACT

Control processes control cross direction alignment of elements being assembled as work pieces on a manufacturing line fabricating preferably absorbent article products on a continuous substrate web. The method defines a manufacturing line path traversed by the work pieces, defines a reference path along the manufacturing path, and establishes the elements on the work pieces. A camera is mounted along the manufacturing line. An image window of the camera is referenced to the reference path. The camera captures full digitized visual images of work pieces. The camera is part of a vision imaging inspection and control system which inspects and evaluates images of the work pieces, including the cross-direction positions of the elements on the work pieces, against established acceptable positions relative to the reference path. When an element is out of alignment, the control system can display visual cues identifying the elements that are inconsistent with acceptable ranges. The full digitized images can be selectively stored in permanent memory, retrieved from permanent memory, and analyzed off-line. The machines are adjusted to adjust positioning of such elements, thereby directing the elements toward target positions. The invention includes step-wise computer-assisted image analysis methodology in an image analysis system linked to a computer program containing system logic, to identify problem areas of the work pieces, and to provide step-wise implementation methodology which can be implemented automatically but is sometimes implemented through human intervention, for making appropriate adjustments to the process. The invention further comprehends apparatus for implementing the above methods, including machines arrayed in a manufacturing line, control apparatus effective to control cross-direction positioning of work pieces, an image collecting system, a memory system, and an image analysis system.

33 Claims, 3 Drawing Sheets

U.S. PATENT DOCUMENTS

| | | | |
|---|---|---|---|
| 4,514,846 A | 4/1985 | Federico et al. | 371/16 |
| 4,577,344 A | 3/1986 | Warren et al. | 382/1 |
| 4,837,715 A | 6/1989 | Ungpiyakul et al. | 364/552 |
| 5,045,135 A | 9/1991 | Meissner et al. | 156/64 |
| 5,138,377 A | 8/1992 | Smith et al. | 355/207 |
| 5,195,029 A | 3/1993 | Murai et al. | 364/184 |
| 5,200,779 A | 4/1993 | Nawata | 355/206 |
| 5,218,406 A | 6/1993 | Ebner | 355/205 |
| 5,239,547 A | 8/1993 | Tomiyama et al. | 371/16.4 |
| 5,251,273 A | 10/1993 | Betts et al. | 382/57 |
| 5,286,543 A | 2/1994 | Ungpiyakul et al. | 428/74 |
| 5,315,697 A | 5/1994 | Nagamatsu | 395/155 |
| 5,333,062 A | 7/1994 | Hara et al. | 358/437 |
| 5,359,525 A | 10/1994 | Weyenberg | 364/469 |
| 5,365,310 A | 11/1994 | Jenkins et al. | 355/202 |
| 5,388,252 A | 2/1995 | Dreste et al. | 395/575 |
| 5,388,618 A | 2/1995 | Decock | 139/1 R |
| 5,392,095 A | 2/1995 | Siegel | 355/200 |
| 5,437,278 A | 8/1995 | Wilk | 128/653.1 |
| 5,452,438 A | 9/1995 | Umeda et al. | 395/180 |
| 5,467,355 A | 11/1995 | Umeda et al. | 364/571.04 |
| 5,490,089 A | 2/1996 | Smith et al. | 364/514 R |
| 5,539,975 A | 7/1996 | Kukuljan et al. | 29/701 |
| 5,564,005 A | 10/1996 | Weber et al. | 395/161 |
| 5,619,445 A | 4/1997 | Hyatt | 365/45 |
| 5,659,538 A | 8/1997 | Stuebe et al. | 364/469.02 |
| 5,694,528 A | 12/1997 | Hube | 395/113 |
| 5,788,802 A * | 8/1998 | Raney | 156/351 |

FOREIGN PATENT DOCUMENTS

| | | | |
|---|---|---|---|
| EP | 0 554 911 A1 | 8/1993 | B32B/31/00 |
| EP | 0 657 852 A2 | 6/1995 | G06T/1/20 |
| EP | 0 738 886 A2 | 10/1996 | G01N/21/00 |
| JP | 9081233 A | 3/1997 | G05B/23/02 |
| WO | WO 93/07445 | 4/1993 | G01B/21/14 |

* cited by examiner

METHOD OF CONTROLLING CROSS-DIRECTION ALIGNMENT IN MANUFACTURING PROCESS

CROSS-REFERENCE TO RELATED APPLICATIONS

This application claims priority to Provisional Application Ser. No. 60/114,482 filed Dec. 31, 1998.

BACKGROUND

This invention relates to apparatus and methods for automatically monitoring and evaluating manufacturing processes, and goods made by manufacturing processes. The invention relates to, for example, operations which produce an ongoing stream of outputs such as discrete absorbent articles, for example disposable diapers, effective to absorb body fluids. Such absorbent article products are typically fabricated as a sequence of work pieces being processed on a continuous web, typically operating on a processing line. Such absorbent article product generally comprises an absorbent core confined between a moisture impervious baffle of e.g. polyethylene and a moisture pervious body side liner of e.g. non-woven fibrous material. The absorbent articles are typically made by advancing one of the webs along a longitudinally extending path, applying the absorbent core to a first one of the webs, and then applying the second web over the combination of the first web and the absorbent core. Other elements such as elastics, leg cuffs, containment flaps, waste bands, and the like are added as desired for the particular product being manufactured, either before, during, or after, applying the second web. Such elements may be oriented longitudinally along the path, or transverse to the path, or may be orientation neutral.

Typically, such manufacturing processes are designed to operate at steady state at a pre-determined set of operating conditions. While such process is operating at steady state conditions, the result desired from the process is desirably and typically achieved. For example, where the process is designed to produce a certain manufactured good, acceptable manufactured goods are normally produced when the process is operating at specified steady state conditions.

As used herein. "steady state conditions" represents more than a single specific set of process conditions. Rather, "steady state" represents a range of specified process conditions which correspond with a high probability that acceptable goods will be produced, namely that the products produced will correspond with specified product parameters.

While a conventional such process is operating, sensors and other monitoring apparatus are typically used individually at various locations along the processing line to automatically sense various respective parameters with respect to, and to otherwise monitor the condition of, the good being manufactured. For example, in a diaper manufacturing operation, a sensor such as a photoelectric eye can be used to sense the presence or absence of a particular element of the diaper such as an ear, the edges of a waist band, the edge or edges of the absorbent core, or the like. In addition, a vision imaging system can be used as another form of sensor to collect and record visual images of, as well as to make measurements on, the units of goods being manufactured.

Known analytical models and control models are based on assumptions that errors related to such sensings, collectings, and recordings are negligible, and thus that all determination signals, or absence of such determination signals, including quantitative signals, as well as the visual images and image analysis measurements made therefrom, are in fact accurate representations of the elements purportedly being detected and/or measured.

However, actual operation of many manufacturing processes, including highly automated processes, typically includes the occurrence of periodic, and in some cases numerous, errors, inaccuracies, or omissions in the determination signals and/or the visual images. Such errors, inaccuracies, or omissions may be caused by any of a variety of factors. Such factors may be, for example and without limitation, complete catastrophic failure of the sensor, intermittent failure of the sensor, error in sensor calibration, a transient out-of-calibration condition of the sensor, an effective obstruction between the sensor and the element to be sensed, or a loose or broken connection between the sensor and the computer or other controller to which the sensor is connected. Such factors also generally apply to vision imaging systems, including the lighting or camera, as well as numerous product component and process irregularities.

A variety of possible events in the manufacturing operation can cause the production of units of product which fall outside the specification range. For example, referring to manufacture of absorbent articles, stretchable materials can be stretched less than, or more than, the desired amount. Elements can become misaligned relative to correct machine direction and/or cross-machine direction registration in the manufacturing operation, or improperly folded over, or creased, or crimped, or torn. Timing between process steps, or speed of advance of an element, can stray from target ranges. If non-catastrophic changes in process conditions can be detected quickly enough, preferably process corrections can be made, and the variances from target conditions can accordingly be controlled such that the product remains within accepted specification ranges, without having to shut down the manufacturing operation, and preferably without having to cull, and thereby waste, product.

A variety of automatic product inspection systems are available for carrying out routine ongoing automatic inspection of product being produced on a manufacturing line, and for periodically and automatically taking samples for back-up manual evaluation. Indeed, periodic manual inspection and evaluation of product samples is still important as a final assurance that quality product is being produced. However, in high-speed manufacturing processes, the primary tool for ongoing real-time product inspection is one or more computer controlled automatic inspection systems which automatically, namely without necessary direct human intervention, inspect the product being manufactured, preferably inspecting every unit of such product.

Where product is outside the accepted specification range, and should be culled, it is desired to cull all defective product, but only that product which is in fact defective. If too little product is culled, or if the wrong product is culled, then defective product is inappropriately released for shipment. On the other hand, if product which in fact meets accepted product specification is culled, then acceptable and highly valuable product is being wasted.

Body-fluid-absorbing absorbent articles such as are of interest herein for implementing the invention are typically manufactured at speeds of about 50 to about 1200 articles per minute on a given manufacturing line. Accordingly, if each unit of product is to be inspected, as here desired, the inspection process must be fast, in order to keep up with the rate of product manufacture here contemplated. Especially at the higher speeds suggested here, it is physically impossible for a typical operator to manually inspect each and every absorbent article so produced. If the operator reacts conservatively, culling product every time he/she has a suspicion, but no solid evidence, that some product may not meet specification, then a significant amount of in-fact-good product will have been culled, and thereby wasted. By contrast, if the operator takes action only when a defect has been confirmed using visual or other manual inspection, defective product may have already been released for shipment before the defective condition has been confirmed.

One way for the operator to inspect the product for conformity with the specification range is for the operator to periodically gather samples of the product being produced, and to inspect such samples off-line. In the manufacture of absorbent articles of particular interest to the inventors herein, such off-line inspection is conventionally practiced by placing the physical product sample on a light table, stretching the product out to its full length and width, and taking desired measurements. Based on the measurements taken, the operator then determines any suitable process adjustments, and implements the respective adjustments.

Random inspections stand little prospect of detecting temporary out-of-specification conditions. On the other hand, where samples are taken by an operator in response to a suspected out-of-specification condition, given the high rate of speed at which such articles are manufactured, by the time the operator completes the inspection, the suspected offensive condition may have existed long enough that a substantial quantity of questionable or defective product will have either been shipped or culled without the operator having any solid basis on which to make the ship/cull decision. Further, automated manufacturing process controls may have self-corrected the defect condition before the operator can take samples, or before the operator can complete the visual/physical inspection and act on the results of such visual inspection. Thus, conventional manual inspection by an operator, while providing the highest potential level of inspection quality holds little prospect of effectively monitoring and controlling temporary out-of-specification conditions, or of pro-actively controlling processing conditions which could produce out-of-specification product, in processes fabricating product at the above-specified rates.

While off-line inspection can be a primary determinant of quality, and typically defines the final quality and disposition of groups of the product, on-line inspection, and off-line evaluation of on-line-collected data, typically associated with certain manufacturing events, may provide valuable insight into both the operational characteristics of the manufacturing process and the final quality parameters of the product, as well as insight into potential proactive improvements which might be made in process control.

Thus, in processes that operate at speeds such that manual inspection of each unit of product is an unrealistic expectation, the primary mechanism for inspecting each unit of product is a computer controlled automatic inspection and control system, optionally including a vision imaging system, backed up by periodic manual inspections of physical samples, or sample images, of product to confirm the accuracy of the decisions being made by the automatic inspection and control system. Such automatic inspection and control system automatically, namely without necessary direct human intervention, inspects the product being manufactured, preferably inspecting each and every unit of such product.

Automatic inspection and control systems rely on a plurality of sensing devices and analytical tools to detect a corresponding plurality of different pre-selected parameters, qualitatively and typically quantitatively, in the goods being produced. Such pre-selected parameters are selected for their prospects of representing the actual overall degree to which the goods conform to pre-selected specifications. The conclusions reached, and the control actions taken on the basis of such conclusions, are only as reliable as the design and implementation of the automatic inspection system, and the accuracy of the determination signals created and/or developed by the respective sensing devices and analytical tools. The reliability of such determination signals is thus critical to the ability of the automatic inspection and control system to sufficiently and efficiently control the manufacturing operation.

While sensors and analytical tools are readily available for use in automatic inspection and control systems, typical such sensors and analytical tools must be carefully manipulated, such as positioned, mounted, calibrated, programmed, and the like, and so maintained in a manufacturing environment.

As a practical matter, such sensors and tools will periodically develop and/or transmit erroneous determination signals, even when managed by a regular maintenance program. In typical situations, the inspection and control system is unable to detect the fact that such signals are erroneous signals, whereby the inspection and control system fails by responding, erroneously, as though the signals were in fact accurate or fails by not responding at all. While the overall purpose of automatic inspection and control is to minimize shipment of defective product, such erroneous response can in fact result in the control system being the cause of product being out-of-specification. Namely, an error in the control system can actually result in release and shipment of product which does not meet accepted specification ranges. So it is critical that the incidence of errors, particularly erroneous determination signals, be limited as much as possible.

As used herein, "erroneous signals" includes signal changes which result from changes in the substrate or other material being sensed by the sensor or tool. For example, if the current supply of the material being sensed has greater or lower opacity than the material for which the sensor or tool is calibrated, then the received signal can give an erroneous indication of the condition of the goods. In such case, and where the inappropriate signal persists, the sensor or tool is preferably recalibrated and/or its sensitivity is adjusted.

As suggested above, there are both advantages and limitations to automatic inspection and control systems. A significant advantage of such systems is that the speed of automatic analysis enables such systems to inspect up to as many as each and every unit being fabricated on manufacturing lines operating at the suggested speeds. Such automatic inspection and control systems are required where rate of product manufacture exceeds the rate of reasonable human/manual inspection.

A limitation of automatic inspection and control systems is that, while such systems conventionally may have the ability to distinguish an accurate determination signal from an erroneous determination signal, they cannot compare, correct, or compensate for, erroneous signals. Further, conventional such systems inspect only a limited portion of the product. And while erroneous signals and readings do not happen often enough to suggest that such automatic inspection and control systems have no net value, to the extent the incidence of erroneous signals can be reduced, or to the extent the incidence of accepting erroneous signals as accurate representations of the overall condition of the product can be reduced, the value of such automatic inspection and control systems will be enhanced.

Where a stream of products is fabricated from a continuous web of substrate material, and wherein a number of elements are established on the substrate web as the web traverses the length of the manufacturing line, it is important that the elements be registered with both the machine direction and the cross-machine direction of the substrate web.

Where elements are to be established on e.g. a substrate web, deviation from proper cross-machine direction registration can result from a deviation of the substrate web or a deviation of the respective element on the web. While a correction of either the web or the element can correct the relative positioning of the element with respect to the web, if the component adjusted was in fact in correct registration with the machines in the manufacturing line before adjustment, the result is that both the adjusted component and the non-adjusted component are then out of registration with the cross-direction alignment of the machines on the manufacturing line. Where more than two components are involved, such correction which takes an additional component, namely the component changed, out of registration with the machines, can also take the additional component out of registration with one or more of the other components.

As an hypothetical example, suppose components 1, 2, and 3 are assembled in a work piece. Components 1 and 2 are out of cross-machine direction registration with respect to each other. Components 1 and 3 are in fact in cross-machine direction registration with the machines and are in proper cross-machine registration with each other. Component 2 is thus out of registration with components 1 and 3 and out of registration with the machines. For purposes of this hypothetical example, the operator notes that components 1 and 2 are out of registration with respect to each other. If the operator adjusts component 2 to component 1, the adjustment works well. If, on the other hand, the operator adjusts component 1 into correct cross-machine direction alignment with component 2, the misalignment of component 2 will not have been corrected, and component 1 will have been taken out of alignment with respect to component 3 and the machines. Where several components are involved, the corresponding several work stations, where the components are established or operations are performed on the work pieces, are potential locations on the manufacturing line for cross-direction alignment adjustments. Thus, several work stations along the manufacturing line provide separate and distinct opportunities for cross-machine adjustment of at least one component, in addition to opportunity for adjustment of the substrate web.

Using current technology, the operator has little basis on which to decide which of the respective components is actually out of cross-direction alignment and/or why. Accordingly, the operator will actually guess which component to adjust, and/or what other corrective action to take without having sufficient technical data to confirm that the decision made is the best decision, or even an appropriate decision. Should the operator guess incorrectly and thus act incorrectly, the result can be to cause relative misalignment of one or more additional components. Further, every time misalignment is found, there is potential for adjusting alignment of the base web. Where alignment of the base web is adjusted improperly, all the components on the web should be adjusted in order that such components not be out of alignment with the substrate web. Each such misalignment of the web provides its own arc in a relatively zig-zag, or snake-like, path along the manufacturing line, rather than the desired path of the substrate web proceeding along a given single plane of advance.

It is an object of this invention to provide improved inspection and control systems, and corresponding methods of measuring cross-direction parameters of the work pieces, which provide improved basis for determining which of the components is misaligned.

It is another object of this invention to provide improved inspection and control systems, and methods of measuring parameters of the product so as to increase reliability of the determination signals created and/or developed by such inspection and control systems.

It is still another object of this invention to provide improved inspection and control systems which evaluate cross-direction position of the respective component with respect to an established reference line, such as a manufacturing path centerline, based on the positions of the machines in the line of manufacturing machines.

It is yet another object to provide for adjusting and/or otherwise correcting the manufacturing process according to deviation from a target specification.

Still another object is to provide inspection and control systems including vision imaging systems establishing the cross-direction positions, with respect to the line of manufacturing machines, of respective components on the work pieces.

Yet another object is to provide such inspection and control systems, the vision imaging systems having suitable system logic capable of calculating corrective action based on a number of measurements taken from representation of a fully digitized image of a work piece on the manufacturing line.

A further object is to provide such inspection and control systems, including vision imaging systems connected to proper control devices such that the inspection and control system automatically makes proper cross-direction adjustment in the manufacturing line to bring the component back toward correct relationship with the reference line.

It is yet another object to provide an inspection and control system wherein the control system interacts with a human operator in determining cross-direction out-of-specification condition, and calculates corrective action to be taken.

It is still another object to provide inspection and control systems which capture digitized full visual images of respective work pieces and, with or without interaction with an operator, inspect the respective visual images for presence and proper positioning of a plurality of components on the work piece.

It is a further object to provide improved inspection and control systems which interact with an operator, leading the operator through a series of computer-aided measurements.

Still another object is to provide inspection and control systems which calculate responses based on the operator's series of computer-aided measurements, and wherein either the operator or the inspection and control system can implement the calculated responses.

Yet another object is to provide inspection and control systems which capture and store digitized full visual images of respective work pieces, and retrieve the full visual images for off-line analysis.

SUMMARY

This invention comprehends a method of controlling cross-machine direction alignment of elements being assembled as work pieces on a manufacturing line having a beginning and an end, and a plurality of work stations to fabricate respective products from the respective work pieces. Preferred work pieces are work pieces being fabricated into absorbent articles such as are mounted on humans for receiving, absorbing and containing human exudates.

The method comprises defining a manufacturing line path traversed by the work pieces as the work pieces move from work station to work station and have work performed thereon; defining a reference path extending along the manufacturing line path, establishing acceptable cross-machine direction positions, relative to the reference path, for an element to be established on each of the work pieces; moving work pieces from work station to work station, and establishing the element on each of the work pieces at respective work stations; fixedly mounting a camera, as a component of a vision imaging inspection and control system, along the manufacturing line path such that the work pieces move past the camera, the camera having an image window defined in terms of images to be captured by the camera and to be displayed by the imaging system; referencing the image window of the camera to the reference path extending along the manufacturing line path; capturing visual images of respective work pieces moving past the camera; and in the captured visual images, evaluating the cross-machine direction position of the element on the respective work pieces with respect to the reference path, against the established acceptable cross-machine direction positions.

In some embodiments, the method includes making adjustment and/or other corrections to appropriate machines on the manufacturing line to thereby adjust cross-machine direction positioning of such elements on subsequent work pieces, to direct the elements toward target cross-machine direction positions.

The invention preferably includes moving the work pieces from work station to work station on a continuous web which is ultimately incorporated into the work pieces as a component of each such work piece.

In preferred implementations of the invention, the product comprises an absorbent article for absorbing body exudates.

Further to preferred embodiments, the reference path represents a centerline of the manufacturing line, and the center line of the manufacturing line corresponds with center lines of the products as the products are being fabricated on the manufacturing line.

In some embodiments, the evaluating comprises direct human intervention in determining at least one measurement.

The invention typically comprehends establishing an acceptable range of cross-machine direction positions for the elements, and taking effective action to prevent defective product from being shipped when the position of one such element is outside the acceptable range. Such effective action can comprise separating defective product from acceptable product by the time the defective product reaches the end of the manufacturing line, providing an alerting signal to the operator that the element is outside the acceptable range, and can include making adjustment to one or more appropriate machines on the manufacturing line to thereby adjust cross-machine direction positioning of such elements on subsequent work pieces, to direct such elements toward target cross-machine direction positions, while providing an alerting signal to an operator and/or separating defective product from acceptable product by the time the defective product reaches the end of the manufacturing line.

Preferred embodiments include capturing full digitized visual images of the respective work pieces.

Especially for use with the full digitized visual images, the invention can include establishing acceptable cross-machine direction positions, relative to the reference path, for each of a plurality of elements, each to be established on each of the work pieces, and instructing the vision imaging inspection and control system to inspect the cross-machine direction positioning of respective ones of the plurality of elements on each of the work pieces.

When an inspected element is inconsistent with a target cross-machine direction position, the invention can make adjustment, or recommend adjustments or other corrective inspections or actions to be taken, at one or more appropriate work stations along the manufacturing line to adjust cross-machine direction positioning of respective such elements on subsequent work pieces of the manufacturing line, to thereby direct the respective elements toward the respective target cross-machine direction position.

In some embodiments, the visual image inspection and control system provides a visual display of respective ones of the work pieces, and provides visual cues identifying elements that are outside acceptable ranges for the respective parameters.

The invention contemplates establishing an acceptable range of cross-machine direction positions, relative to the reference path, for each of a plurality of elements, each to be established on each of the work pieces, and includes taking effective action to prevent defective product from being shipped when the position of a respective element is outside, or otherwise inconsistent with, the respective acceptable range.

Preferred embodiments of the invention include storing, in permanent memory, full digitized visual images of selected ones of the work pieces, retrieving from permanent storage a full digitized visual image representation of one of the stored full digitized visual images, and conducting off-line image analysis of the retrieved image.

The invention preferably includes implementing a preferably step-wise computer-assisted image analysis methodology to assist a system operator in analyzing cross-machine direction positioning of respective elements of the work piece, and in making adjustments, or recommending to the operator adjustments or other corrective inspections or actions to be taken, to direct the process toward alignment of the respective elements along the reference path.

Preferred embodiments include implementing an image analysis system linked to a computer program containing system logic, to identify problem areas of the work piece, and then to provide step-wise implementation methodology for making appropriate adjustments to the process to thereby direct the elements along the reference path.

Some embodiments include the system logic directing operator interaction with the visual image, the operator thus using computer tools to establish a measurement on the visual image, the system logic then applying the so-established measurement by calculating adjustments to be made to the process, and implementing the adjustments at respective locations on the manufacturing line. In some embodiments the system logic makes appropriate adjustments to the process to direct the respective elements for alignment along the reference path. In other embodiments, the system logic advises the operator regarding the calculated adjustments, and the operator then makes appropriate adjustments to the process to direct respective elements suitable for alignment along the reference path.

Preferably the system logic directs sequential steps of operator interaction with the visual image such that the operator makes, and correspondingly identifies to the system logic, a controlled sequence of measurements on the visual image. Based on the controlled sequence of measurements, the system logic subsequently calculates adjustments to be made in the manufacturing operation, and the locations of such adjustments on the manufacturing line. Thus, the operator and the control system work together to make decisions regarding which adjustments are to be made, and to direct such adjustments to the manufacturing operation.

As used herein, "adjustments" refers to the full range of known corrective actions, including such parameters and actions as cleaning, replacing, or rebuilding machines or machine components, especially where operator involvement is indicated in the decision-making process, as well as adjusting on-line parameters such speeds, angles, tensions, and the like on the manufacturing line.

In some embodiments the recited camera is mounted at a first work station, and the invention contemplates fixedly mounting a second camera at a second work station, and capturing second visual images of the respective work pieces moving past the second camera, and using the composite of the first and second visual images to evaluate cross-machine direction positioning of the respective elements.

The invention further comprehends apparatus for controlling cross-machine direction alignment of elements being assembled as e.g. absorbent article work pieces on a manufacturing line, using a manufacturing process. The manufacturing line has a beginning and an end, and a plurality of work stations to fabricate respective products from the respective work pieces. The apparatus comprises manufacturing machines arrayed in a manufacturing line for manufacturing such products; control apparatus effective to control cross-direction positioning, with respect to a reference path, of work pieces traversing the manufacturing line; an image collecting system collecting real-time discrete visual images of the work pieces, at a fixed location in association with said manufacturing machines; a memory storage system receiving selected ones of the real-time visual images; and an image analysis system for display of full digital images as collected by the image collecting system, said image analysis system being linked to a computer program containing system logic for identifying problem areas of respective work pieces so retrieved, and for providing stepwise analysis methodology for identifying problem areas of work pieces.

In preferred embodiments, the image analysis system also makes appropriate adjustments to the process to thereby direct respective elements for suitable alignment along the reference path.

In preferred embodiments, the memory storage system preferably includes high-speed temporary memory storage apparatus, and permanent memory storage apparatus receiving the stored images from the temporary memory storage apparatus.

Preferably, the system is configured to enable the memory storage system to receive a set of visual images concurrent with display of real-time visual images on an image display device.

Also preferably, the image analysis system is linked to the permanent memory storage apparatus for off-line retrieval therefrom of full digitized images as collected by the imaging system.

Figure 1:
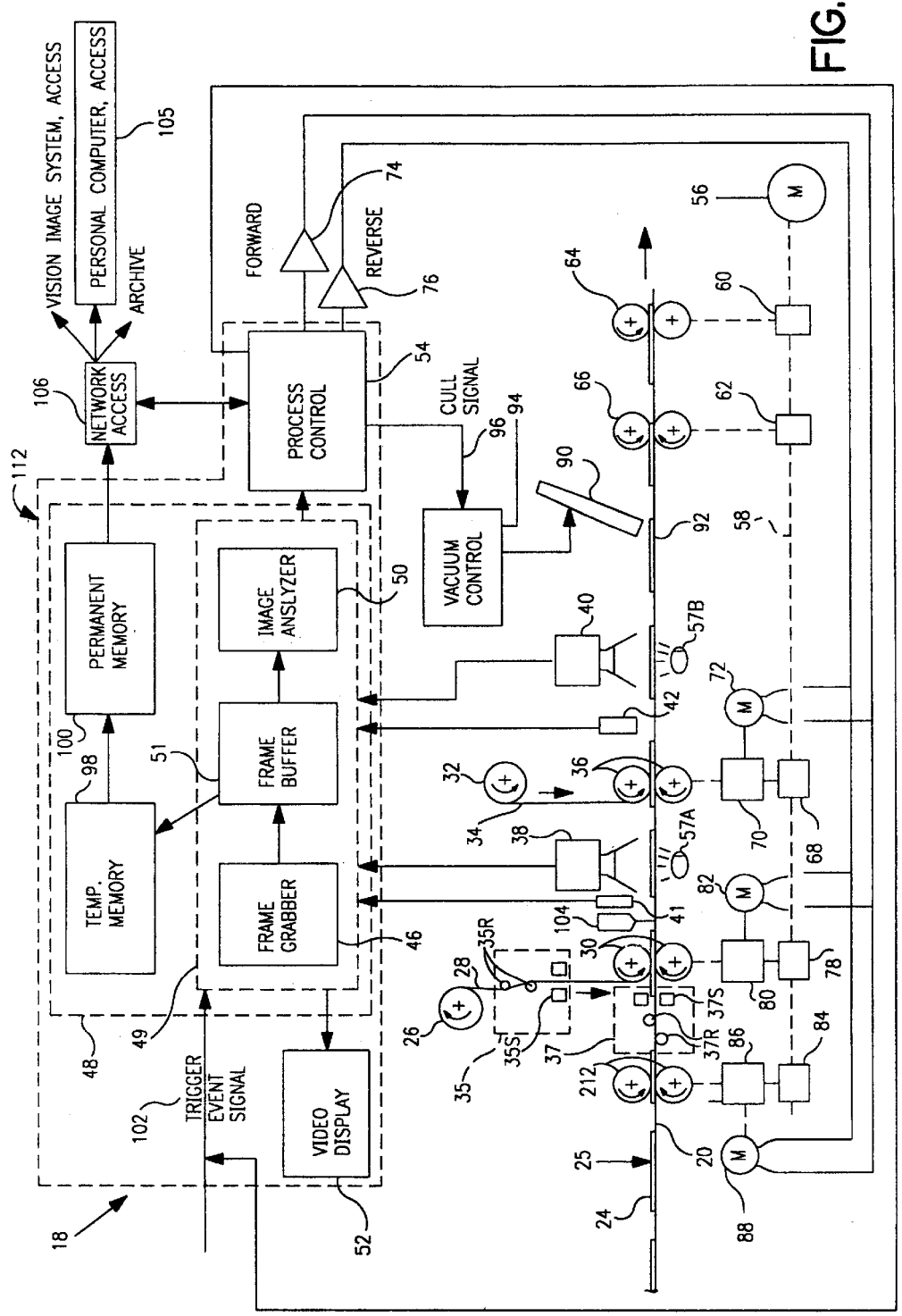
FIG. 1 is a side elevation view of absorbent article manufacturing apparatus of the invention, having an automatic inspection and control system including a vision imaging subsystem comprising image collection, display, and storage apparatus and controls, as well as interface of the vision imaging system with the manufacturing process control system and a memory storage system.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Figure 2:
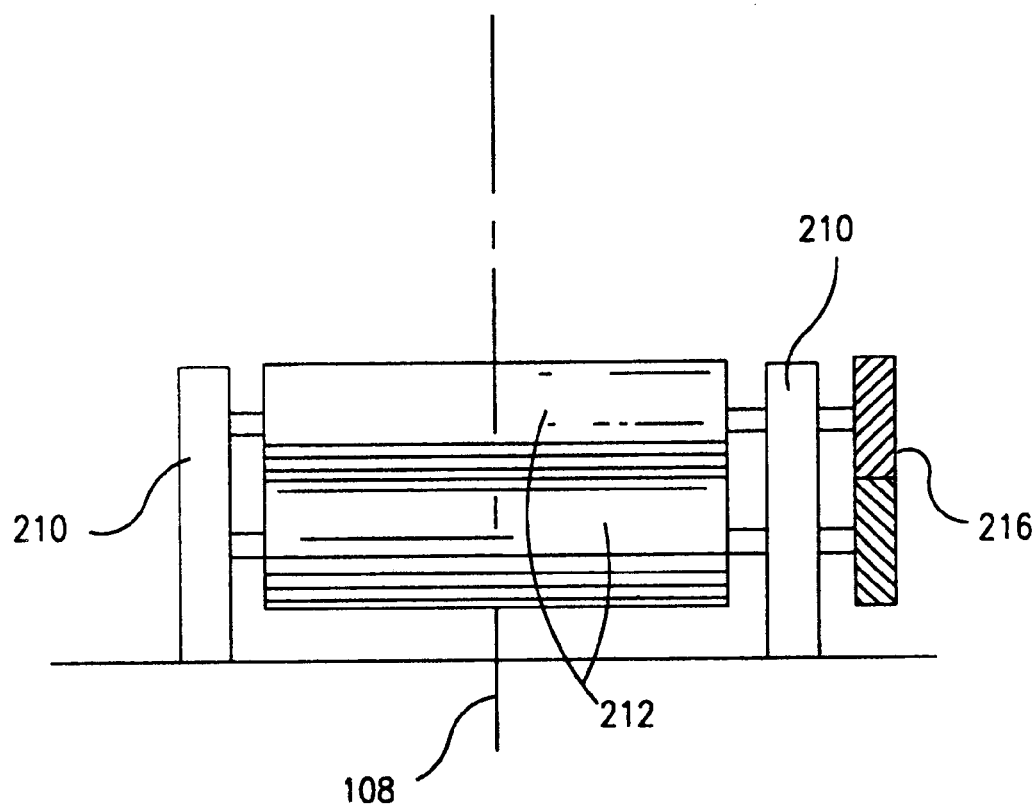
FIG. 2 is a representative end elevation view, also substantially schematic, of a portion of a line of manufacturing machines of FIG. 1, used to make absorbent articles.

With reference to the drawings, and more particularly to FIG. 2, the numeral 210 designates a pair of side frame elements which define a longitudinally extending processing path for the processing of absorbent articles according to the invention. Rotatably mounted on side frames 210 are a pair of processing draw rolls 212 driven by gears 216. Processing draw rolls 212 can be seen toward the left portion of FIG. 1.

Now referring to FIG. 1, absorbent article producing apparatus of the invention is illustrated schematically at 18. Beginning at the left end of FIG. 1, an underlying web 20, for example a moisture impervious baffle web, is shown being advanced toward the right along the longitudinally extending manufacturing path, by draw rolls 212. Omitted for clarity of presentation is the upper confining web such as a body side liner web.

Absorbent pads 24 are shown disposed on web 20 at spaced intervals generally corresponding to the respective separate and distinct work pieces 25 (FIG. 3) or products being fabricated into absorbent articles along the processing path. Additional elements such as leg cuffs, containment flaps, waist bands, and the like are placed, positioned, and otherwise consolidated onto or into continuous web 20, or onto or into each other, at various work stations along the processing path, in the process of fabricating the absorbent articles.

For example, unwind 26 supplies a first web component material such as leg elastics 28 to work station 30 where the web component material is applied on web 20 at rolls 30. Web guide 35, including rolls 35R and sensor 35S, can guide web 28 onto rolls 30 to achieve potential proper position of web 28 on web 20, assuming web 20 is correctly located; and/or web guide 35 can dynamically guide web 28 to the edge of web 20, to the edges of web 20, or to or in accord with another feature of web 20, as provided as control input by web 20 sensor for web guide 35.

Web guide 37, including rolls 37R and sensor 37S, assures that web 20 is properly aligned along the desired path. Process control 54 coordinates and control proper relative alignment of webs 20 and 28 with respect to each other. Similarly, unwind 32 supplies waist band material 34 which is placed on web 20 at rolls 36.

Camera 38 is positioned between the work station defined by rolls 30 and the work station defined by rolls 36. Optional camera 40 is positioned downstream of rolls 36. Once turned on, and so long as they remain turned on, cameras 38, 40 continually collect images and transmit such images to vision system 49. Image trigger device 41 is between rolls 30 and camera 38. Image trigger device 42 is between rolls 36 and camera 40. Cameras 38, 40 communicate with vision system 49 of imaging system 48.

Imaging system 48 includes vision system 49, temporary memory 98, and permanent memory 100. Vision system 49 includes frame grabber 46, frame buffer 51, and image analyzer 50. Image trigger devices 41 and 42 are activated by sensing, for example, the passing of a specific element on each work piece, for example an outwardly-extending ear 44, illustrated in FIG. 3. This activation provides a signal to vision system 49, which sends detect signals to frame grabber 46 and respective strobe light 57A or 57B, also for each work piece. The detect signal thus synchronizes firing of the respective strobe light and corresponding grabbing of the respective frame or image of each respective work piece, then being collected by and transmitted from the respective camera, by frame grabber 46.

Each frame so grabbed is transmitted by frame grabber 46 to frame buffer 51 in registration with movement of the respective work pieces on the manufacturing line such that the frame grabber transfers a visual image of each work piece in accord with detect signals created by the passing of respective work pieces past image trigger devices 41 and 42. While image trigger devices 41 and 42 are illustrated between the rolls and the respective cameras, the trigger devices could be at any location on the processing line which location is compatible with timely collection of frames being recorded by the respective camera or cameras.

Thus, a visual image of each work piece is grabbed and analyzed by vision system 49. Such visual images are sent from frame grabber 46 to frame buffer 51, thence to image analyzer 50 where data analysis is conducted and, upon request by trigger event signal 102, to temporary memory 98. After being processed by vision system 49, the processed camera signal is sent to video image display device 52. The frame grabber, the frame buffer, the image analyzer, the temporary memory, and the permanent memory are all elements of imaging system 48 in the illustrated embodiment.

Figure 3:
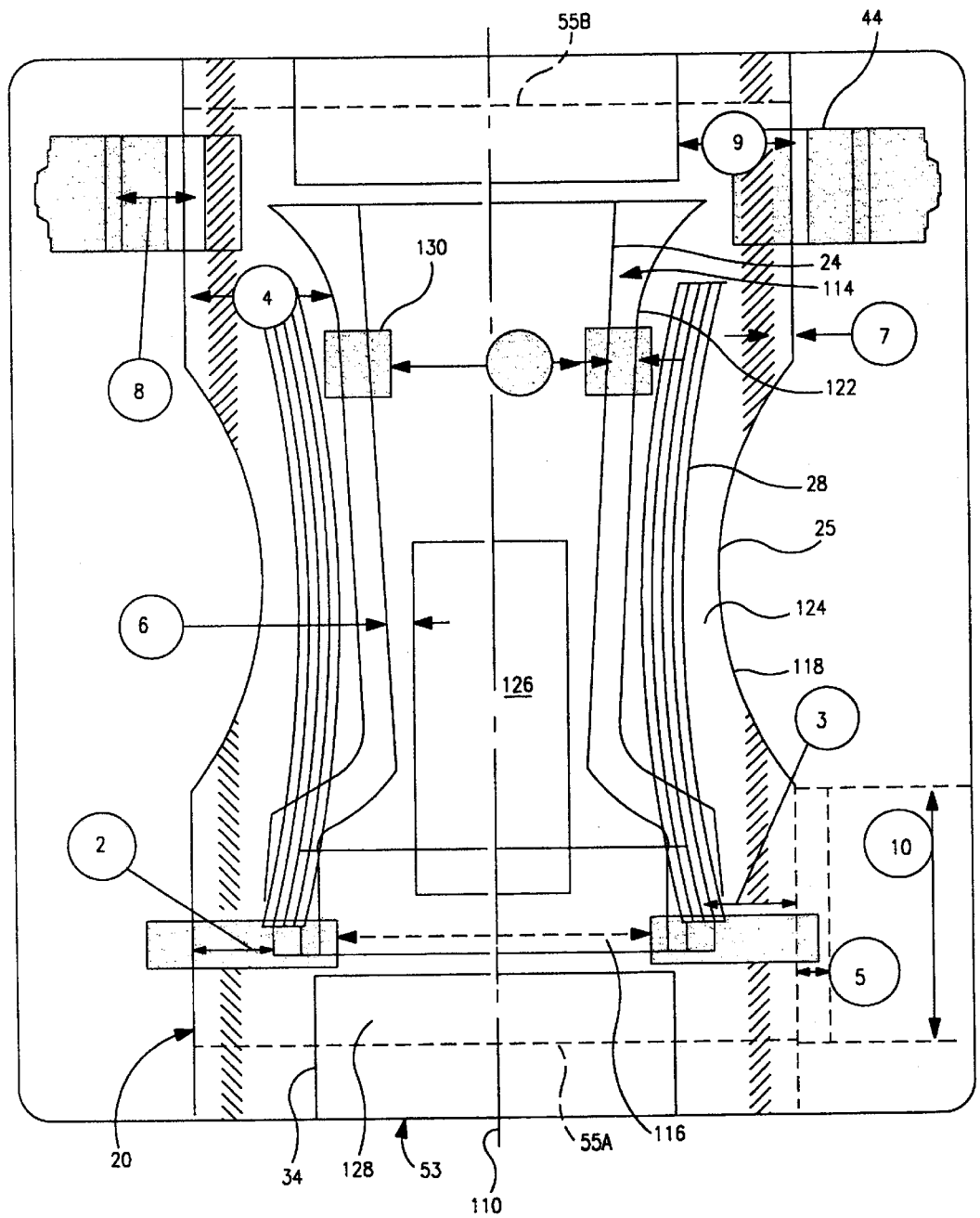
FIG. 3 is a plan view illustrating a typical image of a work piece as displayed to the operator, and including visual cues from the inspection and control system indicating possible out-of-specification areas on the work piece.

Referring to FIG. 3, the closed outline 53 represents the camera field of view or image window, and it will be seen that image window 53 embraces somewhat more than the length of a single work piece 25, but less than the length of two work pieces, disposed generally in the center of image window 53, between projected transverse lines 55A, 55B of future severance, which define the boundaries between sequential work pieces.

Referring now to FIG. 1, a suitable imaging system for use in the invention, including camera, video image display device, frame grabber, and image analyzer, is available from Cognex Corporation, Natick, Mass., USA, as CHECKPOINT 800. Suitable software for collecting, displaying, and analyzing the visual images so collected, of individual ones of the absorbent articles being fabricated in the manufacturing operation, is also available from Cognex Corporation.

The visual image signals collected by camera 38 and optional camera 40 are processed by frame grabber 46 and image analyzer 50. Frame grabber 46 converts the images received from the camera or cameras into digitized representations of the visual images so recorded. Image analyzer 50 analyzes the digitized representations, making a series of measurements according to earlier-programmed software instructions. The results of such analyses can be fed to process control 54 or can be displayed to an operator, along with recommended action steps, whereby the operator makes the final action decisions, and implements the ultimate action steps. Process control 54 receives such signals and issues output commands, as appropriate, to adjust and modify the manufacturing process in order to rectify any anomalous readings and, as appropriate, to steer the manufacturing operation toward pre-selected target specifications stored in process control memory.

Thus, signals may be sent to shift one or more elements in a cross-machine direction on the manufacturing line, to speed up, or slow down, the absolute speed of the manufacturing line, or to advance or retard the timing, of one or more of the process steps at respective work stations in the manufacturing line. Further, signals may be sent to cull product from the manufacturing line and/or to shut the line down.

Referring still to FIG. 1, the number 56 designates the main drive motor which powers the machinery operating the absorbent article production line, which main drive motor is employed to turn a line shaft 58 coupled by gear boxes 60, 62, to draw rolls or turning rolls 64, 66 respectively.

Line shaft 58 is also coupled by gear box 68 to differential 70 which is operated by motor 72 in response to signals from process control 54 through a forward signaling device 74 or a reverse signaling device 76, both of which are coupled to motor 72, to advance or retard the speed of draw of rolls 36, and thereby to advance or retard the speed of flow of work pieces through rolls 36, and accordingly, the relative positioning at which waist band material 34 is applied to the work pieces.

Similarly, line shaft 58 is coupled by gear box 78 to differential 80 which is operated by motor 82 in response to signals from process control 54 through signaling devices 74, 76, both of which are also coupled to motor 82, to advance or retard the relative positioning of work pieces through rolls 30, and accordingly, the relative positioning at which web component material 28 is applied to the work pieces.

Sensor 35S senses the cross machine location of web 28, and sends a signal to e.g. a control (not shown) on roll 35R and/or to process control 54, whereupon a suitable control signal, if any or as appropriate, is sent to guiding roll 35R. Roll 35R is then angularly controlled or adjusted to appropriately guide web 28 in the cross-machine direction. Web guide 37 operates similarly.

Further, line shaft 58 is coupled by gear box 84 to differential 86 which is operated by motor 88 in response to signals from process control 54 through signaling devices 74, 76, both of which are also coupled to motor 88, to advance or retard the speed of draw of work pieces 25 into rolls 12, and accordingly, the speed at which web 20 and the elements resident thereon are fed toward the respective downstream work stations. Additional work stations, not shown, can be employed in similar manner to place and/or affix others of the elements of the absorbent articles, directly or indirectly, onto web 20. In the same manner, line shaft 58 is coupled to respective other gear boxes and differentials as needed elsewhere along the manufacturing line in order to provide machine direction drive and speed control at the various work stations.

After an image has been analyzed by analyzer 50 and has been processed by process control 54, correction logic embodying the range of specifications acceptable for the work piece can be delivered to signaling devices 74 (forward) and/or 76 (reverse) for advancing or retarding the respective manufacturing actions, or to vacuum control 94 for culling work pieces.

Vacuum shoe 90 is positioned over work station 92 downstream of camera 40, and is controlled by vacuum control 94. In circumstances wherein the signals received by process control 54 indicate that the work piece which was imaged and analyzed is outside accepted specification range, process control 54 can send a cull signal 96 to vacuum control 94, activating vacuum to vacuum shoe 90 at the appropriate time to cull the individual work piece which gave the out-of-specification information. Where desired, and where suitable lead time is available to the cull system, vacuum control 94 can be programmed to cull, in addition, a specified number of work pieces before and/or after the work piece which yielded the out-of-specification visual image information.

In addition to providing an output to process control 54, vision system 49, on demand, also outputs visual image information to high speed temporary memory 98 which subsequently outputs the visual image information to permanent memory 100. The visual image information inputted from vision system 49 to temporary memory 98, and subsequently to permanent memory 100, is sufficient in quantity and satisfactory in quality and specificity, to generally re-create the individual images collected by camera 38 and/or camera 40. Thus, the stored information maintains substantially the full integrity, typically full digital integrity, of the visual images so stored, so as to be fully representative of the images recorded or collected by camera 38 or 40. Accordingly, the visual images so stored enable the user to substantially reproduce the respective images which were available to the operator in real-time during manufacturing of the respective absorbent articles.

A temporary memory suitable for general purpose use in association with the invention is a VME memory card having memory capacity of up to about 1 Gigabyte, and 152 is available from Chrislin Industries Inc. Westlake Village, Calif., USA. Such temporary memory can capture, and store in memory, visual images of typical absorbent articles such as those described herein, at the high capture/store rate of at least about 500 images per minute, up to about 1000 images per minute, potentially up to about 1200 images per minute.

Communication between vision system 49 and temporary memory device 98 requires use of a suitable protocol such as a VME standard to transfer data across the computer backplane or other link to a temporary memory device. Such a temporary memory is a VME bus standard IEEE 1014.

For permanent storage to be effected, it is critical that the visual image information received in the high-speed temporary memory storage, e.g. buffer, device be expeditiously transferred to a permanent memory storage device. A typical suitable permanent memory storage device is, for example and without limitation, a hard drive such as hard drives commonly used in personal computers. Where a larger amount of memory is desired than is available on a conventionally-available hard drive, a combination of such hard drives can be coupled together in well known manner to thereby provide the composite capacity of all the hard drives so coupled together. While a computer hard drive has been indicated, any memory apparatus which similarly retains the information in retrievable and usable form for a prolonged period of time when power is withdrawn from the device, is an acceptable permanent memory storage apparatus.

The value of temporary memory device 98 is to enable high speed real-time transfer of the visual image information from the imaging system. Conventional permanent memory devices are too slow for such real-time transfer at any reasonable interface cost, whereby the temporary memory device is used.

The value of permanent memory 100 is three-fold. First, once the information has been received into permanent memory, such permanent memory can be accessed by a variety of users, if desired, through a typical networked computer interface system. Second, permanent memory retains the information in memory when power is turned off and wherein power is disconnected from the permanent memory storage device, and power is thus lost. Thus, once the visual image information is disposed in permanent memory, the risk of loss from removal or interruption of power supply is obviated. Third, permanent memory is less costly than temporary e.g. buffer memory.

Accordingly, images which conventionally have been available only to the operator on the manufacturing line, and which have been available only as real-time images, are now available at any time, to anyone having access to the permanent memory device, such as from a remote computer terminal through, and remote from, network access 106. Similarly, the data from automatic analyses done by image analyzer 50 and stored in process control 54 can be polled and accessed from a remote terminal such as personal computer 105, through network access 106, thus allowing direct correlation and comparison of specific images with specific process control information. The images accordingly remain available for real-time use at the manufacturing line, as before; and can, in addition, be accessed either on or off the manufacturing floor at a later time by any authorized user, for further analysis at whatever level of analysis is desired.

Thus, visual images of the product, or the process, can be permanently archived, and associated with specific manufacturing periods or specific manufacturing events, without interrupting ongoing collection of such visual images. In addition, the visual images so stored in memory can be re-created from the stored data in the same or another vision system, or can be stored and re-used in other software applications such as in combination with bit-map systems. However stored, and however retrieved, such retrieved information can be used for in-depth analysis of the results, on the work pieces, of specific events occurring on the manufacturing line as well as analyses of the products produced on the manufacturing line.

Individual images recorded or received at cameras 38, 40, and ultimately stored in permanent memory 100, can be accessed individually from permanent memory 100, and analyzed as desired, any time after the respective images are stored in permanent memory. For example, an analyst can choose to review and analyze a certain set of images based on the occurrence of a triggering event, or a set of images recorded, according to the time at which the images were collected. As is well known for use of such computer memory devices, visual image data which is permanently stored in e.g. permanent storage device 100 can be written over or erased at will in order to make such storage space available for use to store other information, for example, later-produced data.

The above described imaging system 48 has a rate capacity capable of producing a visual image of each and every work piece produced by the manufacturing operation at speeds up to 1200 images per minute. Indeed, it is desirable to the line operator that the imaging system does produce a visual image of each and every work piece, and does permanently record certain data pertaining to each and every work piece. However, such routine measurement data recorded by the imaging system conventionally comprises only results-type information related to the visual image, for example certain distance measurements, and bears no capability to recreate the actual image.

It is not practical to store a full visual image, pixel-by-pixel, of each and every work piece. Such storage of all visual images so produced would require an inordinate amount of storage capacity in memory device 100. In addition, since the rate of production of such images is greater than the input rate capacity of a typical hard drive permanent memory storage device to receive such information, such storage would have to be carried out in parallel with multiple permanent memory devices concurrently receiving memory storage inputs. Still further, the amount of data so stored in memory would make it difficult for an inquirer to identify images of particular interest for further study and/or to correlate any such images with specific events in the manufacturing process. Thus, efficient searching, sorting, and retrieval of visual image information suggests at least an initial sorting of such images prior to storage so as to store only those images having a relatively higher probability of containing information which will be valuable during subsequent data analysis.

Accordingly, it is important that full digitized visual images be transferred from frame buffer 51 to a memory storage device such as temporary buffer memory 98 only upon the occurrence of selected, preferably predetermined, triggering events. By limiting transfers to memory to only those images associated with certain triggering events or other higher-risk events, the amount of storage media required is appropriately limited to a manageable amount, and the amount of data stored, and which may be reviewed to find evidence of an event of interest, is also limited so as to be manageable.

The suggested Cognex imaging system can be programmed to transfer to memory a specified number of visual images upon the occurrence of a specified triggering event. The transfer can begin so as to take samples wherein the work piece being imaged when the triggering occurred is at or toward the beginning of the sample, in the midst of the sample, or at or toward the end of the sample.

The user can specify, as a triggering event for collection of visual image data, any event of interest which can be identified to process control and captured by the camera. For example, a splice in any of feed webs 20, 28, 34 might be specified as a triggering event. A certain amount of change in line speed might be specified as a triggering event. A certain amount of change in tension of one or more webs might be specified as a triggering event. An out of specification condition might be specified as a triggering event. Additionally, a manual trigger can be used to initiate image capture, as can a timer, or a random number generator.

However the triggering event is created or triggered, manufacturing controls are configured such that, upon the occurrence of a triggering event, a signal 102 is generated. e.g. by a sensor or by a process control command, and transmitted to vision system 49, triggering frame buffer 51 to begin sending visual images to memory, and specifying how many images are to be sent to memory.

Thus, upon the occurrence of a triggering event, a defined set of a limited number of real-time visual images so collected by frame grabber 46 is sent to temporary memory device 98. While information is still being received by temporary memory device 98, memory device 98 may begin transferring the visual image information to permanent memory device 100 at the slower rate at which the permanent memory device is capable of receiving and storing such information.

Accordingly, in preferred embodiments, part of the visual image information has already been transferred to permanent storage device 100 by the time the last of the set of images has been received in high speed memory 98. Accordingly, memory device 98 acts as an accumulator to temporarily take up the excess volume of visual images being transferred from vision system 49, until memory device 100 can receive the balance of the set of images.

Should a second triggering event occur before the last ones of the first set of images has been transferred to memory device 100, temporary memory device 98 receives the second set of images, and transfers such second set of images to memory device 100 after, optionally concurrently with, completing transfer of the first set of images. In some embodiments, such first and second sets of visual images are segregated from each other, as separate and distinct sets of image information, in at least one of the respective memory storage devices.

Upon completion of transfer of a given set of visual images according to a triggering event, preferably no more visual images are transferred to memory devices 98, 100 until the next triggering event occurs. While a few visual images may be routinely transferred to storage memory during routine operation of the process, for historical record-keeping purposes, e.g. to keep an historical record of product made and/or shipped, or for e.g. routine detailed off-line evaluation, e.g. by an operator, the number of images collected in sequence for each sampling is significantly less, namely less than 10%, preferably less than 2%, as many as the number of images which are stored in accord with the occurrence of a typical triggering event.

A typical set of images includes images of about 1 to about 1000 consecutive work pieces in the manufacturing line. Images of up to about 200 work pieces per set are contemplated for typical use in the invention. Storing greater than about 1000 images of work pieces per set mentioned will inordinately increase storage costs, albeit computer memory, and may create a database so large that finding useful information may be difficult, or at least inefficient. Larger sets of work piece images can, of course, be stored if the resources requirements are justified by the particular set of facts.

The illustrated embodiments indicate use of one or two cameras 38, 40. Typically, use of one camera is adequate to indicate the strengths or weaknesses of the manufacturing operation. However, where an anomaly exists, or is difficult to correct, or where e.g. more information is desired for any reason, additional cameras, such as camera 40, can be set up at the same or corresponding additional locations along the manufacturing line, and connected into the imaging system 48, and the memory system (device 98 and device 100), in order to collect and permanently store additional information. Accordingly, the imaging system can produce and store in memory a second set of data, either before, e.g. shortly before, during, or after, e.g. shortly after, collecting and storing a first set of data. The second set of data can be obtained from the same camera, e.g. directed at the same location on the processing line, as the first set of data, or can be obtained from a second camera pointed at the same location on the processing line or located at a different work station, recording a different step in the process.

By associating suitable identification indicia with each transfer of a set of visual images to storage, the reviewing artisan can search first for the identification indicia, and having found the identification indicia, can then focus on the parameters of interest associated with the respective visual images.

Where it is desired to correlate specific physical samples to the visual images of such samples, an article-specific code, different for each work piece so coded, can be printed on the respective work pieces 25, as at, for example, ear 44. Such code can be marked, for example printed, by e.g. a non-contact, e.g. ink-jet, printer 104 located up-stream of the respective camera such that the code appears both on the physical unit of product and on the visual image of that unit of product. In the alternative, a common code, specific to the triggering event, can be printed on each work piece associated with the triggering event.

While not critical to the invention, it is preferred that the visual images sent to memory devices 98, 100 be the same images sent to display device 52. In such instances, the images available for review later are the same images which were available for display to the operator in real time.

In some instances, the images sent to memory may not have been sent to display device 52. Especially where images are being taken at more than one location on the manufacturing line, at least some of the images stored may not have been sent to display device 52. However, in general, it is contemplated that the operator would have the option of viewing any images being recorded at any given time. Where more than one camera is taking images, none, some, or all of the images can be made available to the operator for viewing, and some or all of the images can be sent to permanent storage. As indicated herein before, preferably, only selected sets of images are sent to permanent storage.

The invention has been described above generally in terms of known or planned triggering events. However, imaging system 48 can be programmed to trigger storage of visual images in memory upon the occurrence of a wide variety of unplanned events, for example, any occurrence of any out-of-specification event, or any other unplanned event, as well as routine sampling.

In some embodiments, the trigger signals collect visual images of fewer than all of the work pieces being processed in the manufacturing operation. Where desired, the imaging system can be programmed to collect images of every second work piece, every third work piece, or any other desired fraction of the work pieces. Such selection can collect images at regular intervals, or at selected intermittent intervals. For example, the imaging system might be programmed to command taking images of a certain set/number of sequential work pieces, for example 3 work pieces, then skip the next set of work pieces, for example 5 work pieces. The actual interval between work pieces whose images are recorded, and the pattern of which work piece images are to be collected, is a matter of selection for the artisan setting up the image collection.

As used herein, "absorbent article" refers to a class of products worn on the human body, and used generally for promotion of human hygiene by the absorption of body fluids and other exudates. Examples of such absorbent articles include, without limitation, diapers, training pants, incontinence pads, feminine hygiene pads, interlabial pads, and the like.

As used herein, a "high speed" memory storage device is a storage device capable of receiving at least about 50, preferably at least about 200, and more preferably at least about 300, still more preferably at least 400 or 500, up to at least about 1200, visual images per minute from cameras of the nature described herein for use in the invention, and must be able to track the unit rate of production of products of interest to the imaging system. Commonly available such memory devices are variously known as Random Access Memory devices, and/or Buffer Memory devices, both terms being well known in the art. Typically available such memory storage devices retain the data only so long as power is maintained on such devices, and wherein any data stored therein is lost when electrical power is terminated. Accordingly, such memory devices are not suitable for permanent storage of data. Rather, in the invention the data is written from the high speed temporary storage device to a lower speed, permanent memory storage device.

The number of images collected per minute is controlled by signals, from the processing line, indicating the frequency of passage along the processing line, of work pieces whose images are to be collected.

As used herein, a "lower speed" memory storage device is any memory storage device which is unable to receive visual images of absorbent article-type products from frame buffer 51 of the nature described herein for use in the invention, usually at a rate of less than about 500 visual images per minute. Typical such memory devices are hard drives such as are commonly employed in personal computers. Such hard drives are available in a variety of sizes, and in a range of input speeds, wherein large amounts of image data can be readily stored in permanent memory, at reasonable cost per image, albeit at lower input rates.

The number of images which can be transferred over a given unit of time is a function of the complexity of the image inspections, and the resolution of the images. The more complex the image inspection and/or the higher the image resolution, the slower the transfer rate capacity of the vision system 49.

As used herein, reference to a "generally fixed" location where visual images are collected means that the image collection element such as a camera is fixedly mounted to a physical support, and is directed to a specific step or steps at a specific work station in the manufacturing operation. Thus, "generally fixed" refers to a camera fixed in location but with capability to digitally or optically zoom the image to facilitate inspection of certain elements of the work piece or work pieces, while not moving the camera from its mounted location. The cameras can, of course, be moved and subsequently recalibrated.

Preferably, the camera is fixed in both location and direction of aim, such that sequentially collected images represent common location and common direction of aim, of the camera.

As used herein, "pattern of images" refers to an ongoing selection of images according to a selection pattern. The selection pattern can select, and therefore collect, an image specific to each work piece, product, or process condition. The selection pattern can, in the alternative, select and collect an image according to an alternative pattern, for example collecting an image of every second or every third work piece, product, or process condition, or collecting an image of every work piece, product, or process condition for a limited number of images, at regularly-spaced, or otherwise determined, intervals. The above-described patterns are exemplary only, and not limiting, as other patterns are now obvious and viable in the invention.

Referring to FIGS. 2 and 3, methods of the invention are based on establishing a reference path, such as a reference line, for traverse of the manufacturing operation. Such reference line is based on the path of advance of work pieces along the line of machines, irrespective of any positioning of any one work piece with respect to the machines. Namely, the reference line is completely defined in terms of the manufacturing line of machines. FIG. 2 shows an imaginary vertical plane 108 extending along a centerline of the line of machines, and defining a reference line for purposes of inspection and control systems of the invention. In this example, plane 108 extends parallel to the line of advance of work pieces traversing along the manufacturing line. For purposes of the remainder of this discussion plane 108 will be referred to as line 108, it being remembered that 108 represents generally a line in a plane.

Line 108 can extend at an angle to the line of advance of work pieces, but such would complicate the analysis of cross-direction positioning of the work pieces, and thus is not preferred. Similarly, line 108 can be positioned at a location other than along the center of the manufacturing line. For example, line 108 can be positioned at the right or left edges of the manufacturing line as viewed in FIG. 2, or offset to the left or right of, and completely separated from, the manufacturing line. All that is required is that the position of the reference line be established to the inspection and control system along the length of the manufacturing line.

Referring now to FIG. 3, line 110 defines an imaginary centerline of image window 53 extending along the machine direction of the manufacturing line. In the illustrated embodiment, in calibration of the respective camera 38 or 40, image window 53 is referenced to reference line 108 such that all elements in an image can be referenced directly to centerline 110 and thus indirectly to reference line 108, since centerline 110 is aligned with, and resides in, line 108 along the full length of the manufacturing line when the line of work pieces is properly aligned in the cross-machine direction along the full length of the manufacturing line.

In setting up the manufacturing operation, the distance of the centerline from the reference line can be entered into the process control memory. More importantly, certain acceptable ranges of distances are entered into the process control memory. Namely, the distance between the centerline and a cross-direction edge of each component of the work piece is entered into process control memory. For example, where as here the centerline of the image window coincides with the centerline of the product work piece being fabricated, and the reference line of the manufacturing line, process control can simply look for centering of the absorbent core with respect to centerline 110. In practice of the invention, an edge of the work piece web can be referenced to the reference line, rather than an element of the image window being referenced to the reference line.

The distances entered into process control represent both an acceptable range of distances for each component and a target distance. The target distance is used as a target for making minor ongoing adjustments to the process in order to optimize product quality. The acceptable range for a distance represents accept/reject decision boundaries such that when the product violates one of the boundaries the product is culled.

FIG. 3 illustrates the type of decisions which process control 54 is called upon, and is equipped, to make. The following items 1–10 represent measurements that control system 112 (FIG. 1) makes in the illustrated example. The numerals on FIG. 3 are circled in order to readily distinguish process system measurements from structural elements of the work piece.

Thus, item 1 represents the query whether absorbent core 24 is centered with respect to centerline 110 and tissue 114.

Item 2 represents the query whether fastener landing zone substrate 116 is centered with respect to centerline 110 and outer cover 118.

Item 3 represents the query whether leg elastics 28 are centered with respect to centerline 110 and outer cover 118.

Item 4 represents the query whether tissue edge 122 is centered with respect to centerline 110 and outer cover 118.

Item 5 represents the query whether body side liner 124 is centered with respect to centerline 110 and outer cover 118.

Item 6 represents the query whether surge material 126 is centered with respect to centerline 110 and absorbent core 24.

Item 7 represents the query whether the overall sausage is centered with respect to centerline 110 and bonders which establish and thus bond ears 44 to the work piece.

Item 8 represents the query whether ears 44 are properly displaced from centerline 108 and from each other.

Item 9 represents the query whether the diaper sausage is properly centered with respect to centerline 108 and with respect to the applicator of waist piece 128.

Item 10 represents the query whether the diaper sausage is properly centered with respect to centerline 108 and the sausage cutter.

Other items can as well be queried, on this or another product, for conformance to pre-programmed measurement standards. Thus the items actually queried can be more than, or less than, and can be different from, the 10 items illustrated in FIG. 3.

Based on the visual images grabbed by frame grabber 46, and the values previously entered in control system 112, image analyzer 50 can detect the position of respective edges of each of the above respective components of the diaper, and can compute distances representative of the measurements desired.

Preferably, however, such in-depth analysis is performed off-line on images which have been previously stored in permanent memory 100. However, and under whatever conditions analyzed, based on the computed distances, control system 112 can make two levels of decisions. First, control system 112 can make an accept/reject decision to hold certain product for further e.g. manual inspection. Where the decision is to reject, preferably control system 112 automatically identifies the respective work pieces, also for further e.g. manual inspection.

Where the decision is to accept, or where a parameter is so close to a reject decision as to represent a higher than normal risk, the control system sends an alert signal to alert an operator of the condition of the work piece. FIG. 3 illustrates such an alert signal as a visual cue where two square patches 130 on the visual image are stippled and bordered by the control system, to indicate that the item 1 query, centering of absorbent core 24 with respect to tissue 114 needs individual back-up inspection. The circle about the numeral "1" is also stippled to call attention to I& the requested back-up inspection.

A similar visual alert signal is seen at 2 in FIG. 3, to indicate that the item 2 query, whether landing zone 116 is centered with respect to centerline 110 and outer cover 118, needs back-up inspection. Where so desired, control system 112 can be programmed so as to enable the control system to issue corrective action commands through process control 34 and/or to separate actual or suspect product, or high risk product, from low risk product by the time the respective higher risk units of product reach the end of the manufacturing line, all while displaying the indication that back-up inspection is needed.

Referring again to FIG. 1, vision system 49 can be programmed to output to the operator real time images and associated analysis information related to the work pieces being concurrently produced. Such real time display is updated with the passing of each work piece. Such display gives the operator an overview of the product being produced, but does not enable the operator, or other investigator, to inspect any one work piece in any detail.

In the alternative, the video display can be programmed to freeze the frame any time an anomaly condition is defined by the automatic inspection and control system, or where one or more positions are sufficiently unclear to the sensors in the control system that they cannot be automatically read and analyzed. Where an anomalous condition is defined by control system 112, and images are stored in memory, the operator has a number of options, including accepting or rejecting the unit of product. In addition, the operator can retrieve stored images and use the computer mouse to point and click on respective edges of components in order to define to the control system the edges as perceived by the operator.

Once the distances have been so defined, control system 112 calculates suggested corrective actions, and transmits the suggested corrective actions to the operator, or if so programmed, implements the respective corrective actions at appropriate work stations on the manufacturing line by making adjustment to appropriate machines at one or more work stations or other locations on the manufacturing line to thereby adjust cross-machine direction positioning of such elements on subsequent work pieces, thus to direct the components toward target cross-machine direction positions.

In the alternative, video display can be maintained as a real-time display while the respective visual images are brought up on a second display screen associated with a personal computer such as the computer indicated at 105 in FIG. 1. Such retrieval from memory is likely to be less time sensitive, but allows for analysis of images at a more relaxed pace, whereby the analysis can be a more in-depth study of the image.

As used herein, "off-line" image analysis refers to the timing and/or depth of analysis of the respective image. Either the image is retrieved from permanent memory or an on-line collected image is analyzed in such depth, for such a period of time, that a corrective instruction to the process, based solely on the image analyzed, would be inappropriate. However, if the improper condition is persistent, the result from off-line analysis may still suggest an on-line, real-time adjustment of operating conditions.

Within the context of the above described cross-direction sensing and control, the invention contemplates automatic (that is machine-initiated and/or machine-controlled) analysis and control, as well as manual (that is operator-initiated and/or operator-controlled) analysis and control, of the cross machine positioning of web 20. The invention further contemplates that such automatic and manual analysis and control can coexist concurrently, such that the operator can modify and/or override any adjustments made, or to be made, by the automatic analysis and control system.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A method of controlling cross-machine direction alignment of elements being assembled as work nieces on a manufacturing line, the manufacturing line including a plurality of work stations, to fabricate respective products from the respective work pieces, the method comprising:

(a) defining a machine direction manufacturing line path traversed by the work pieces as the work nieces move from work station to work station and have work performed thereon;

(b) defining a machine direction reference path extending in the direction of the machine direction manufacturing line path and referenced to machines along the manufacturing line;

(c) establishing acceptable cross-machine direction positions along the manufacturing line path and relative to the reference path, for an element to be established on respective ones of the work pieces;

(d) moving work pieces from work station to work station, and establishing the element on the respective work pieces at respective work stations;

(e) fixedly mounting a camera, as a component of a vision imaging inspection and control system, alone the manufacturing line path such that the work pieces move past the camera, the camera having an image window defined in terms of images to be captured by the camera and to be displayed by the imaging system;

(f) referencing the image window of the camera to the reference path;

(g) capturing visual images of respective work pieces moving past the camera; and (h) in the captured visual images, evaluating the cross-machine direction position of the element on the respective work pieces with respect to the reference path, against the established acceptable cross-machine direction positions, wherein the reference path represents a centerline of the manufacturing line.

2. A method as in claim 1, the center line of the manufacturing line corresponding with center lines of the products as the products are being fabricated on the manufacturing line.

3. A method of controlling cross-machine direction alignment of elements being assembled as work pieces on a manufacturing line, the manufacturing line including a plurality of work stations, to fabricate respective products from the respective work pieces, the method comprising:

(a) defining a machine direction manufacturing line path traversed by the work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions along the manufacturing line path and relative to the reference path, for an element to be established on respective ones of the work pieces;

(d) moving work pieces from work station to work station, and establishing the element on the respective work pieces at respective work stations;

(e) fixedly mounting a camera, as a component of a vision imaging inspection and control system, along the manufacturing line path such that the work pieces move past the camera, the camera having an image window defined in terms of images to be captured by the camera and to be displayed by the imaging system;

(f) referencing the image window of the camera to the reference path;

(g) capturing visual images of respective work pieces moving past the camera; and (h) in the captured visual images, evaluating the cross-machine direction position of the element on the respective work pieces with respect to the reference path, against the established acceptable cross-machine direction positions, the evaluating of step (h) comprising direct human intervention in determining at least one measurement.

4. A method of controlling cross-machine direction alignment of elements being assembled as work pieces on a manufacturing line, the manufacturing line including a plurality of work stations, to fabricate respective products from the respectively work pieces, the method comprising:

(a) defining a machine direction manufacturing line path traversed by the work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions along the manufacturing line path and relative to the reference path, for an element to be established on respective ones of the work pieces;

(d) moving work pieces from work station to work station, and establishing the element on the respective work pieces at respective work stations;

(e) fixedly mounting a camera, as a component of a vision imaging inspection and control system, along the manufacturing line path such that the work pieces move past the camera, the camera having an image window defined in terms of images to be captured by the camera and to be displayed by the imaging system;

(f) referencing the image window of the camera to the reference path;

(g) capturing visual images of respective work pieces moving past the camera; and (h) in the captured visual images, evaluating the cross-machine direction position of the element on the respective work pieces with respect to the reference path, against the established acceptable cross-machine direction positions, including capturing full digitized visual images of the respective work pieces, the visual image inspection and control system providing a visual display of respective ones of the work pieces, and providing visual cues identifying elements that are outside acceptable ranges for the respective parameters.

5. A method as in claim 4, including establishing an acceptable range of cross-machine direction positions, relative to the reference path, for each of a plurality of elements, each to be established on each of the work pieces, and including taking effective action to prevent defective product from being shipped when the position of a respective element is inconsistent with the respective acceptable range.

6. A method as in claim 5 wherein the effective action comprises separating defective product from acceptable product by the time the defective product reaches the end of the manufacturing line.

7. A method as in claim 5 wherein the effective action comprises providing an alerting signal to an operator.

8. A method as in claim 5 wherein the effective action comprises adjusting cross-machine direction positioning of such elements on subsequent work pieces, to direct the elements toward target cross-machine direction positions, while providing an alerting signal to an operator and/or separating defective product from acceptable product by the time the defective product reaches the end of the manufacturing line.

9. A method of controlling cross-machine direction alignment of elements being assembled as work pieces on a manufacturing line, the manufacturing line including a plurality of work stations, to fabricate respective products from the respective work pieces, the method comprising:

(a) defining a machine direction manufacturing line path traversed by the work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions along the manufacturing line path and relative to the reference path, for an element to be established on respective ones of the work pieces;

(d) moving work pieces from work station to work station, and establishing the element on the respective work pieces at respective work stations;

(e) fixedly mounting a camera as a component of a vision imaging inspection and control system, along the manufacturing line path such that the work pieces move past the camera, the camera having an image window defined in terms of images to be captured by the camera and to be displayed by the imaging system;

(f) referencing the image window of the camera to the reference path;

(g) capturing visual images of respective work pieces moving past the camera; and (h) in the captured visual images, evaluating the cross-machine direction position of the element on the respective work pieces with respect to the reference path, against the established acceptable cross-machine direction positions, including storing, in permanent memory, full digitized visual image representation of selected ones of the work pieces, retrieving from permanent storage a full digitized visual image representation of one of the stored full digitized visual images, and conducting off-line image analysis of the retrieved image, including implementing a computer-assisted image analysis methodology to assist a system operator in analyzing cross-machine direction positioning of respective elements of the work piece, including implementing step-wise computer analysis methodology to assist the system operator in making adjustments to direct the process toward alignment of the respective elements along the reference path.

10. A method as in claim 9, including activating stepwise computer directed implementation methodology and thereby making appropriate adjustments to the process to thereby direct the elements along the reference path.

11. A method of controlling cross-machine direction alignment of elements being assembled as work pieces on a manufacturing line the manufacturing line including a plurality of work stations, to fabricate respective products from the respective work pieces, the method comprising:

(a) defining a machine direction manufacturing line path traversed by the work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions along the manufacturing line path and relative to the reference path, for an element to be established on respective ones of the work pieces;

(d) moving work pieces from work station to work station, and establishing the element on the respective work pieces at respective work stations;

(e) fixedly mounting a camera, as a component of a vision imaging inspection and control system, along the manufacturing line path such that the work pieces move past the camera, the camera having an image window defined in terms of images to be captured by the camera and to be displayed by the imaging system;

(f) referencing the image window of the camera to the reference path;

(g) capturing visual images of respective work pieces moving past the camera; and (h) in the captured visual images, evaluating the cross-machine direction position of the element on the respective work pieces with respect to the reference path, against the established acceptable cross-machine direction positions, including storing in permanent memory, full digitized visual images of selected ones of the work pieces, retrieving from permanent storage a full digitized visual image representation of one of the stored full digitized visual images, and conducting off-line image analysis of the retrieved image, including implementing a computer-assisted image analysis methodology to assist a system operator in analyzing cross-machine direction positioning of respective elements of the work piece, including implementing an image analysis system linked to a computer program containing system logic effective to identify problem areas of the work piece and to then provide step-wise implementation methodology for making appropriate adjustments to the process, to thereby direct the elements along the reference path consistent with acceptable cross-direction positioning of the respective elements.

12. A method as in claim 11, wherein the system logic assists the operator in making appropriate adjustment decisions to thereby direct the elements for suitable cross-direction alignment along the reference path.

13. A method as in claim 12, including the system logic directing operator interaction with the visual image, the operator thus using computer tools to establish a measurement on the visual image, the system logic then applying the so-established measurement by calculating adjustments to be made to the process, and advising the operator regarding the calculated adjustments, the operator then making appropriate adjustments to the process to direct respective elements suitable for alignment along the reference path.

14. A method as in claim 13, the operator and the system logic working together to make the ultimate decision regarding which adjustments are to be made, and directing such adjustments to the manufacturing operation.

15. A method as in claim 11, including the system logic directing operator interaction with the visual image, the operator thus using computer tools to establish a measurement on the visual image, the system logic then applying the so-established measurement by calculating adjustments to be made to the process, and implementing the adjustments at respective locations on the manufacturing line, to make appropriate adjustments to the process to direct the respective elements for alignment along the reference path.

16. A method as in claim 15, including the system logic directing sequential steps of operator interaction with the visual image such that the operator makes, and correspondingly identifies to the system logic, a controlled sequence of measurements on the visual image.

17. A method as in claim 16, including, based on the controlled sequence of measurements, the system logic subsequently calculating adjustments to be made in the manufacturing operation, and the locations of such adjustments on the manufacturing line.

18. A method as in claimed the operator and the system logic working together to make the ultimate decision regarding which adjustments are to be made, and directing such adjustments to the manufacturing operation.

19. A method of controlling cross-machine direction alignment of elements being assembled as work pieces on a manufacturing line, the manufacturing line including a plurality of work stations, to fabricate respective products from the respective work pieces, the method comprising:

(a) defining a machine direction manufacturing line path traversed by the work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions along the manufacturing line path and relative to the reference path, for an element to be established on respective ones of the work pieces;

(d) moving work pieces from work station to work station, and establishing the element on the respective work pieces at respective work stations;

(e) fixedly mounting a camera, as a component of a vision imaging inspection and control system, along the manufacturing line path such that the work pieces move past the camera, the camera having an image window defined in terms of images to be captured by the camera and to be displayed by the imaging system:

(f) referencing the image window of the camera to the reference path;

(g) capturing visual images of respective work pieces moving past the camera; and (h) in the captured visual images, evaluating the cross-machine direction position of the element on the respective work pieces with respect to the reference path, against the established acceptable cross-machine direction positions, the camera being mounted at a first work station, and including fixedly mounting a second camera at a second work station, and capturing second visual images of the respective work pieces moving past the second camera, and using the composite of the first and second visual images to evaluate cross-machine direction positioning of the respective elements with respect to the reference path.

20. A method of controlling cross-machine direction alignment of elements being assembled as work pieces on a manufacturing line, the manufacturing line including a plurality of work stations, to fabricate respective absorbent article products from the respective work pieces, the method comprising:

(a) defining a machine direction manufacturing line path traversed by the absorbent article work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions along the manufacturing line path and relative to the reference path, for an element to be established an respective ones of the absorbent article work pieces;

(d) moving absorbent article work pieces from work station to work station, and establishing the element on of the respective absorbent article work pieces at respective work stations;

(e) fixedly mounting a camera, as a component of a vision imaging inspection and control system, along the manufacturing line path such that the absorbent article work pieces move past the camera, the camera having an image window defined in terms of images to be captured by the camera and to be displayed by the imaging system;

(f) referencing the image window of the camera to the reference path;

(g) capturing visual images of respective absorbent article work pieces moving past the camera; and (h) in the captured visual images, evaluating the cross-machine direction position of the element on the respective absorbent article work pieces with respect to the reference path, against the established acceptable cross-machine direction positions, wherein the reference path represents a centerline of the manufacturing line.

21. A method as in claim 20, the center line of the manufacturing line corresponding with center lines of the absorbent article products being fabricated on the manufacturing line.

22. A method of controlling cross-machine direction alignment of elements being assembled as work pieces on a manufacturing line, the manufacturing line including a plurality of work stations, to fabricate respective absorbent article products from the respective work pieces, the method comprising:

(a) defining a machine direction manufacturing line path traversed by the absorbent article work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions alone the manufacturing line path and relative to the reference path, for an element to be established on respective ones of the absorbent article work pieces;

(d) moving absorbent article work pieces from work station to work station, and establishing the element on of the respective absorbent article work pieces at respective work stations;

(e) fixedly mounting a camera, as a component of a vision imaging inspection and control system, along the manufacturing line path such that the absorbent article work pieces move past the camera, the camera having an image window defined in terms of images to be captured by the camera and to be displayed by the imaging system;

(f) referencing the image window of the camera to the reference path;

(g) capturing visual images of respective absorbent article work pieces moving past the camera; and (h) in the captured visual images, evaluating the cross-machine direction position of the element on the respective absorbent article work pieces with respect to the reference path, against the established acceptable cross-machine direction positions, the evaluating of step (h) comprising direct human intervention in determining at least one measurement.

23. A method of controlling cross-machine direction alignment of elements being assembled as work pieces on a manufacturing line, the manufacturing line including a plurality of work stations, to fabricate respective absorbent article products from the respective work pieces, the method comprising:

(a) defining a machine direction manufacturing line path traversed by the absorbent article work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions alone the manufacturing line path and relative to the reference path, for an element to be established on respective ones of the absorbent article work pieces;

(d) moving absorbent article work pieces from work station to work station, and establishing the element on of the respective absorbent article work pieces at respective work stations;

(e) fixedly mounting a camera, as a component of a vision imaging inspection and control system, along the manufacturing line path such that the absorbent article work pieces move past the camera, the camera having an image window defined in terms of images to be captured by the camera and to be displayed by the imaging system;

(f) referencing the image window of the camera to the reference path;

(g) capturing visual images of respective absorbent article work pieces moving past the camera; and (h) in the captured visual images, evaluating the cross-machine direction position of the element on the respective absorbent article work pieces with respect to the reference path, against the established acceptable cross-machine direction positions, including capturing full digitized visual images of the respective work pieces, the visual image inspection and control system providing a visual display of respective ones of the work pieces, and providing visual cues identifying elements that are outside acceptable ranges for the respective parameters.

24. A method as in claim, including establishing an acceptable range of cross-machine direction positions, relative to the reference path, for each of a plurality of elements, each to be established on each of the work pieces, and including taking effective action to prevent defective product from being shipped when the position of a respective element is inconsistent with respective acceptable range.

25. A method of controlling cross-machine direction alignment of elements being assembled as work pieces on a manufacturing line, the manufacturing line including a plurality of work stations, to fabricate respective absorbent article products from the respective work pieces, the method comprising:

(a) defining a machine direction manufacturing line path traversed by the absorbent article work pieces as the work pieces move from work station to work station and have work performed thereon;

(b) defining a machine direction reference path extending in the direction of the machine direction manufacturing line path and referenced to machines along the manufacturing line;

(c) establishing acceptable cross-machine direction positions along the manufacturing line path and relative to the reference path, for an element to be established on respective ones of the absorbent article work pieces;

(d) moving absorbent article work pieces from work station to work station, and establishing the element on of the respective absorbent article work pieces at respective work stations;

(e) fixedly mounting a camera, as a component of a vision imaging inspection and control system, along the manufacturing line path such that the absorbent article work pieces move past the camera, the camera having an image window defined in terms of images to be captured by the camera and to be displayed by the imaging system;

(f) referencing the image window of the camera to the reference path;

(g) capturing visual images of respective absorbent article work pieces moving past the camera; and (h) in the captured visual images, evaluating the cross-machine direction position of the element on the respective absorbent article work pieces with respect to the reference path, against the established acceptable cross-machine direction positions, including storing, in permanent memory, full digitized visual images of selected ones of the work pieces, retrieving from permanent storage a full digitized visual image representation of one of the stored full digitized visual images, and conducting off-line image analysis of the retrieved image, including implementing a computer-assisted image analysis methodology to assist a system operator in analyzing cross-machine direction positioning of respective elements of the work piece, including implementing step-wise computer analysis methodology to assist the system operator in making adjustments to direct the process toward alignment of the respective elements along the reference path.

26. A method as in claim 25, including activating step wise computer directed implementation methodology and thereby making appropriate adjustments to the process to thereby direct the elements along the reference path.

27. A method of controlling cross-machine direction alignment of elements being assembled as work pieces on a manufacturing line, the manufacturing line including a plurality of work stations, to fabricate respective absorbent article products from the respective work pieces, the method comprising:

(a) defining a machine direction manufacturing line path traversed by the absorbent article work pieces as the work pieces move from work station to work station and have work performed thereon;

(b) defining a machine direction reference path extending in the direction of the machine direction manufacturing line path and referenced to machines alone the manufacturing line;

(c) establishing acceptable cross-machine direction positions along the manufacturing line path and relative to the reference path, for an element to be established on respective ones of the absorbent article work pieces;

(d) moving absorbent article work pieces from work station to work station, and establishing the element on of the respective absorbent article work pieces at respective work stations;

(e) fixedly mounting a camera, as a component of a vision imaging inspection and control system, along the manufacturing line path such that the absorbent article work pieces move past the camera, the camera having an image window defined in terms of images to be captured by the camera and to be displayed by the imaging system;

(f) referencing the image window of the camera to the reference path;

(g) capturing visual images of respective absorbent article work pieces moving past the camera; and (h) in the captured visual images, evaluating the cross-machine direction position of the element on the respective absorbent article work pieces with respect to the reference path, against the established acceptable cross-machine direction positions, including storing, in permanent memory, full digitized visual images of selected ones of the work pieces, retrieving from permanent storage a full digitized visual image representation of one of the stored full digitized visual images, and conducting off-line image analysis of the retrieved image, including implementing a computer-assisted image analysis methodology to assist a system operator in analyzing cross-machine direction positioning of respective elements of the work piece, including implementing an image analysis system linked to a computer program containing system logic effective to identify problem areas of the work piece and to then provide step-wise implementation methodology for making appropriate adjustments to the process, to thereby direct the elements along the reference path consistent with acceptable cross-direction positioning of the respective elements.

28. A method as in claim 27 wherein the system logic assists the operator in making appropriate adjustment decisions to thereby direct the elements for suitable cross-direction alignment along the reference path.

29. A method as in claim 28, including the system logic directing operator interaction with the visual image, the operator thus using computer tools to establish a measurement on the visual image, the system logic then applying the so established measurement by calculating adjustments to be made to the process, and advising the operator regarding the calculated adjustments, the operator then making appropriate adjustments to the process to direct respective elements suitable for alignment along the reference path.

30. A method as in claim 29, the operator and the system logic working together to make the ultimate decision regarding which adjustments are to be made, and directing such adjustments to the manufacturing operation.

31. A method as in claim 27, including the system logic directing operator interaction with the visual image, the operator thus using computer tools to establish a measurement on the visual image, the system logic then applying the so-established measurement by calculating adjustments to be made to the process, and implementing the adjustments at respective locations or the manufacturing line, to make appropriate adjustments to the process to direct the respective elements for alignment along the reference path.

32. A method as in claim 31, including the system logic directing sequential steps of operator interaction with the visual image such that the operator makes, and correspondingly identifies to the system logic, a controlled sequence of measurements on the visual image and, based on the controlled sequence of measurements, the system logic subsequently calculating adjustments to be made in the manufacturing operation, and the locations of such adjustments on the manufacturing line.

33. Apparatus for controlling cross-machine direction alignment of a web suitable for use in fabricating absorbent articles, and with which web elements are being assembled to form work pieces on a manufacturing line, using a manufacturing process, the manufacturing line including a plurality of work stations to fabricate respective products from the respective work pieces, said apparatus comprising:

(a) apparatus defining a machine direction manufacturing line path traversed by the work pieces as the work pieces move from work station to work station and have work performed thereon;

(b) sensing apparatus for sensing transverse direction positioning, with respect to the reference path, of the web or an element to be established on the web at respective ones of the work pieces;

(c) web guide apparatus for controlling transverse direction positioning, with respect to the reference path, of the web or an element to be established on the web at respective ones of the work pieces; and (d) process control apparatus having a memory, and defining, in such memory, a machine direction reference path extending in the direction of the machine direction manufacturing line path and referenced to machines along the manufacturing line, and establishing acceptable cross-machine direction positions, relative to the reference path, for the web or an element to be established on the web at respective ones of the work pieces.

* * * * *